(12) United States Patent
McGeer et al.

(10) Patent No.: US 10,966,945 B2
(45) Date of Patent: *Apr. 6, 2021

(54) SELECTIVE INHIBITION OF THE MEMBRANE ATTACK COMPLEX OF COMPLEMENT BY LOW MOLECULAR WEIGHT COMPONENTS OF THE AURIN TRICARBOXYLIC SYNTHETIC COMPLEX

(75) Inventors: Patrick L. McGeer, Vancouver (CA); Moonhee Lee, Vancouver (CA); Jian-Ping Guo, Vancouver (CA); Claudia Schwab, Burnaby (CA)

(73) Assignee: Aurin Biotech Inc., Vancouver (CA)

( * ) Notice: Subject to any disclaimer, the term of this patent is extended or adjusted under 35 U.S.C. 154(b) by 688 days.

This patent is subject to a terminal disclaimer.

(21) Appl. No.: 13/195,216

(22) Filed: Aug. 1, 2011

(65) Prior Publication Data

US 2013/0035388 A1 Feb. 7, 2013

(51) Int. Cl.

| A61K 31/194 | (2006.01) |
|---|---|
| A61P 25/00 | (2006.01) |
| A61P 25/28 | (2006.01) |
| A61P 9/10 | (2006.01) |
| A61P 27/02 | (2006.01) |
| A61P 33/06 | (2006.01) |

(52) U.S. Cl.
CPC .......... *A61K 31/194* (2013.01); *A61P 25/00* (2018.01); *A61P 25/28* (2018.01); *A61P 9/10* (2018.01); *A61P 27/02* (2018.01); *A61P 33/06* (2018.01)

(58) Field of Classification Search
CPC ......... A61K 31/194; A61P 25/00; A61P 25/28
See application file for complete search history.

(56) References Cited

U.S. PATENT DOCUMENTS

| 4,007,270 | A | * | 2/1977 | Bernstein et al. ............ 514/159 |
| 4,880,788 | A | | 11/1989 | Moake |
| 5,434,185 | A | | 7/1995 | Parikh |
| 6,538,028 | B1 | | 3/2003 | Pierson, III et al. |
| 2013/0035392 | A1 | | 2/2013 | McGeer |

FOREIGN PATENT DOCUMENTS

| CA | 2631071 A1 | 11/2009 |
| WO | 01/57184 A2 | 8/2001 |
| WO | 2007/062186 A1 | 5/2007 |
| WO | 2010/042728 A1 | 4/2010 |

OTHER PUBLICATIONS

U.S. Appl. No. 13/541,535, filed Jul. 2013, McGeer et al.*
Wang et al. J. Org. Chem. 1992, vol. 57, pp. 3861-3866.*
Rogers et al. PNAS, vol. 89, pp. 10016-10020, Nov. 1992.*
Anderson, D.H., et al., "A role for location inflammation in the formation of drusen in the aging eye", Am J Ophthamol, 2002, 134(3):411-431.
Anderson, D.H., et al., "The pivotal role of the complement system in aging and age-related macular degeneration: hypthesis revisited", Prog Ret Eye Res, 2010, 29:95-112.
Cushman, M., et al., "Synthesis of the covalent hydrate of the incorrectly assumed structure of aurintricarboxylic acid", Tetrahedron, 1990, 46(5):1491-1498.
Cushman, M., et al,. "Synthesis and anti-HIV activities of low molecular weight aurintricarboxylic acid fragments and related compounds", J Med Chem, 1991, 34(1):337-342.
Cushman, M., et al., "Structural investigation and anti-HIV activities of high molecular weight ATA polymers", J Org Chem, 1992, 57(26):7241-7248.
Gonzalez, R.G., et al., "Fractionation and structural elucidation of the active components of aurintricarboxylic acid, a potent inhibition of protein nucleic acid interactions", Biochimica et Biophysica Acta, 1979, 562:534-545.
Heisig, G.B., et al., "Ammonium salt of aurin tricarboxylic acid", Organic Syntheses, 1941, 1:54.
Kira, S., et al., "Nonsense mutation in exon 4 of human complement C9 gene is the major cause of Japanese complement C9 deficiency", Human Gen, 1998, 102(6):605-610.
Lee, M., et al., "Astrocyctes are GABAergic cells that modulate microglial activity", Glia, 2011, 59(1):152-165.
McGeer, P.L., et al., "Activation of the classical complement pathway in brain tissue of Alzheimer patients", Neuroscience Letters, 1989, 107:341-346.
Owens, M.R., et al., "Aurin tricarboxylic acid inhibits adhesion of platelets to subendothelium", Thrombosis Res, 1996, 81(2):177-185.
Yasojima, K., et al., "Generation of C-reactive protein and complement components in atherosclerotic plaques", American J Pathol, 2001, 158(3):1039-1051.
Benezra, M., et al., "Antiprolifrative activity to vascular smooth muscle cells and receptor binding of heparin-mimicking polyaromatic anionic compounds", Arterioscler Thromb Vasc Biol, 1994, 14:1992-1999.
Cushman, M., et al., "Preparation and anti-HIV activities of aurintricarboxylic acid fractions and analogues, direct correlation of antiviral potency with molecular weight", J Med Chem, 1991, 34:329-337.
Cushman, M., et al,. "Synthesis and anti-HIV activities of low molecular weight aurintricarboxylic acid fragments related and compounds", J Med Chem, 1991, 34(1):337-342.
Genain, C.P., et al., "Identification of autoantibodies associated with myelin damage in multiple sclerosis", Nat Med, 1999, 5(2):170-175.

(Continued)

*Primary Examiner* — Kara R McMillian
(74) *Attorney, Agent, or Firm* — Oyen Wiggs Green & Mutala LLP

(57) ABSTRACT

This patent pertains to selective inhibition of assembly of the membrane attack complex of complement by use of less than 1 kDa molecular weight forms of the aurin tricarboxylic acid synthetic complex (ATAC), and their derivatives. It further pertains to the use of these materials to treat human conditions where there is evidence of self destruction of host tissue by the membrane attack complex. These diseases include, but are not limited to, Alzheimer disease, age related macular degeneration, and atherosclerosis.

6 Claims, 14 Drawing Sheets

(56) References Cited

OTHER PUBLICATIONS

Figure 1:
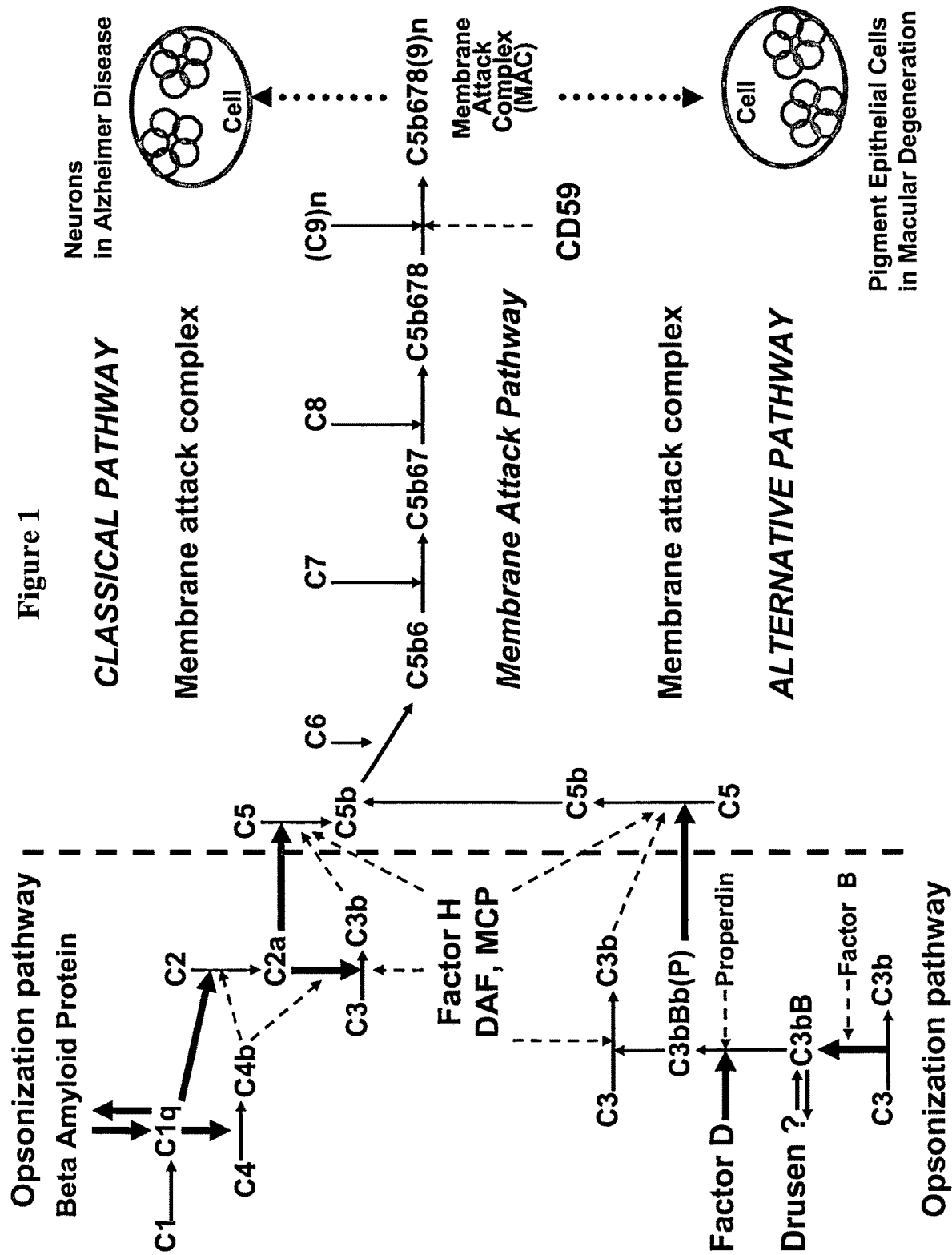

Hillmen, P., et al., "The complement inhibitor eculizumab in paroxysmal nocturnal hemoglobinuria", N Engl J Med, 2006, 355(12):1233-1243.
Lapidus, M., et al., "New inhibitors of complement fixation", Immunopharmacology, 1981, 3:137-145.
Lee, M., et al., "Selective inhibition of the membrane attack complex of complement by low molecular weight components of the aurin tricarboxylic acid synthetic complex", Neurobiol Aging, 2012, 33(10):2237-2246.
Okroj, M., et al., "Rheumatoid arthritis and the complement system", Ann Med, 2007, 39(7):517-530.
Parker, C.J., "Paroxysmal nocturnal hemoglobinuria", Curr Opin Hematol, 2012, 19(3):141-148.
Silver, K.L., et al., "Complement driven immune responses to malaria: fuelling severe malarial disease", Cellular Microbiol, 2010, 12(8):1036-1045.
Tan, S., et al., "Oxidative stress induces a form of programmed cell death with characteristics of both apoptosis and necrosis innauronal cells", Journal of Neurochemistry, 1998, 71:95-105.
Ingram et al., "Complement in multiple sclerosis: its role in disease and potential as a biomarker", Clin. Exp. Immunol., 2009, 155(2), pp. 128-139.
Aurintricarboxylic acid inhibits endothelial activation, complement activation, and von Willebrand factor secretion in vitro and attenuates hyperacute rejection in an ex vivo model of pig-to-human pulmonary xenotransplantation; Hyun Kyung Kim; Ji-Eun Kim; Hyun Cho Wi; Sang Woo Lee; Ji Yeon Kim; Hee Jung Kang; Young Tae Kim; Xenotransplantation: 2008, vol. 15, Issue 4, pp. 246-256.
Hyperacute lung rejection in the pig-to-human model platelet receptor inhibitors synergistically modulate complement activation and lung injury; Steffe Pfeiffer et al., Transplantation: 2003—vol. 75, Issue 7, pp. 953-959.

\* cited by examiner

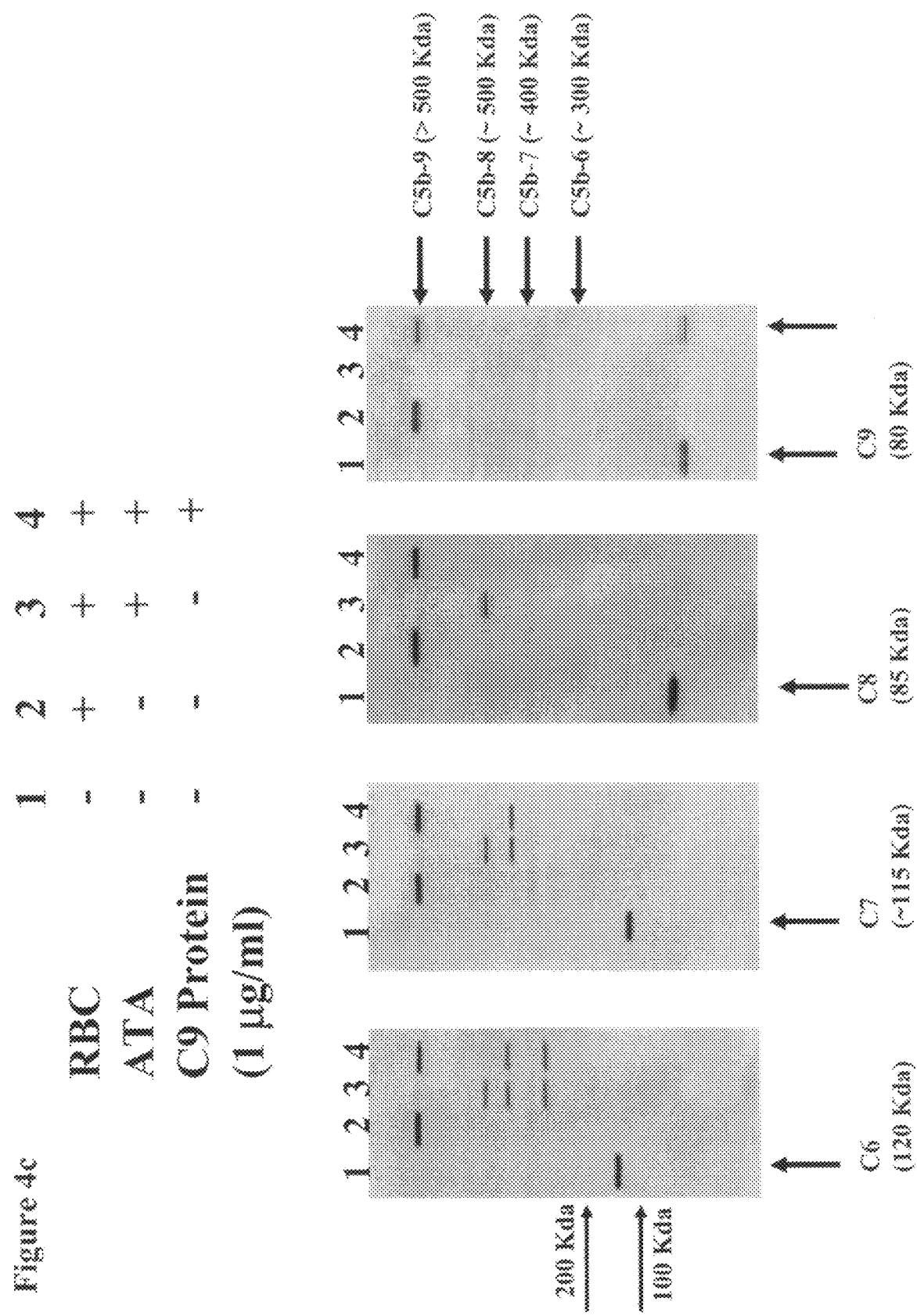

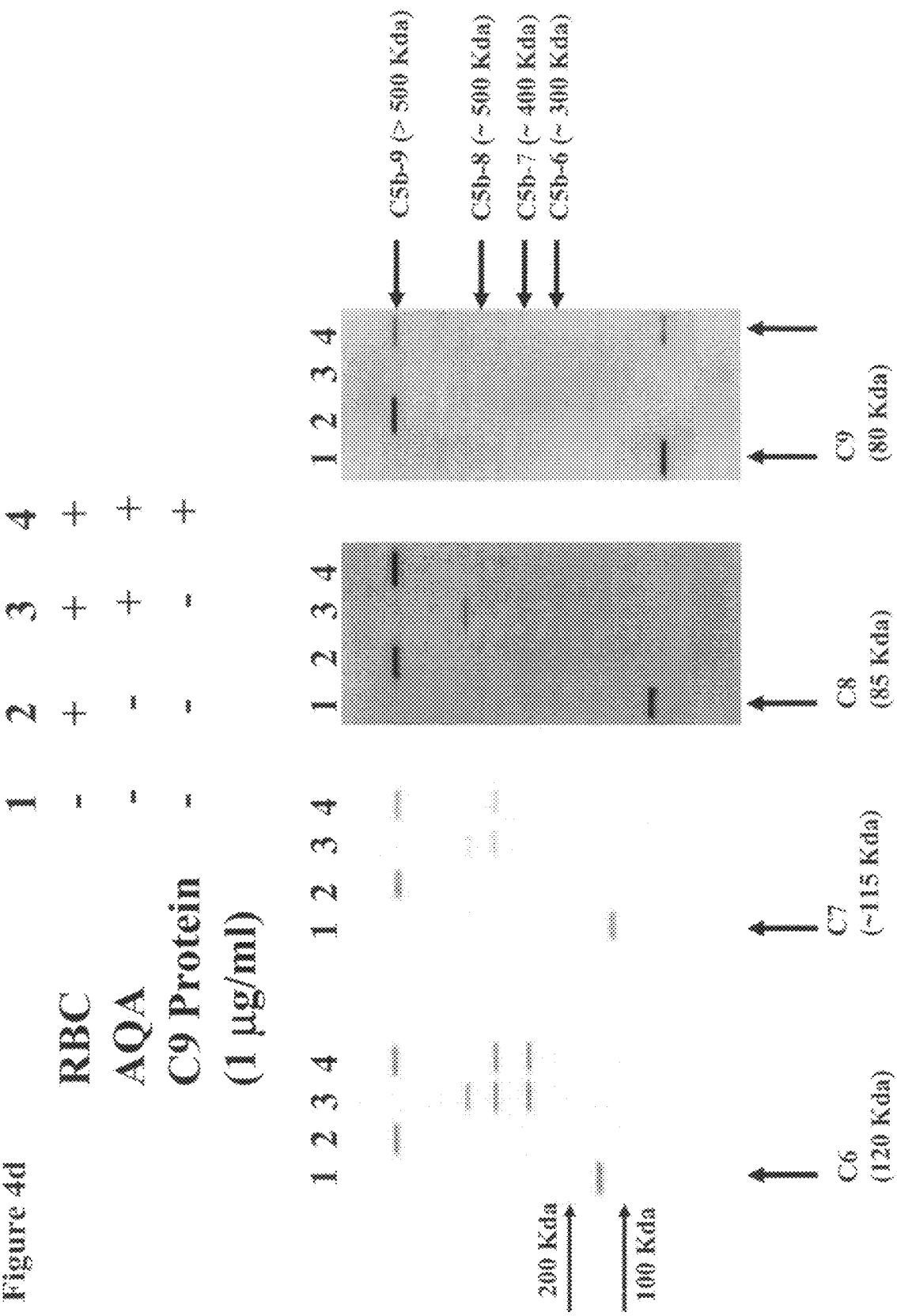

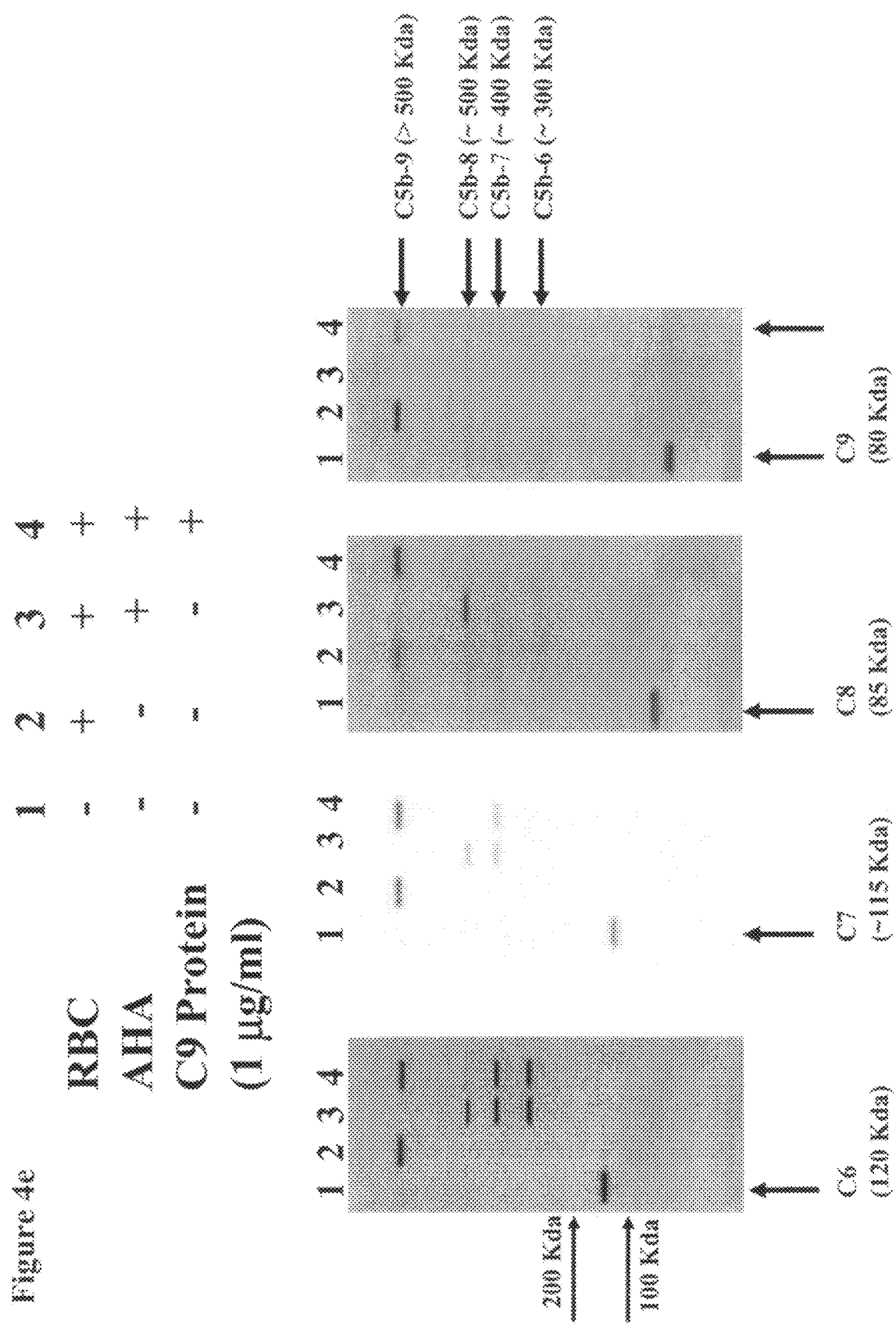

SELECTIVE INHIBITION OF THE MEMBRANE ATTACK COMPLEX OF COMPLEMENT BY LOW MOLECULAR WEIGHT COMPONENTS OF THE AURIN TRICARBOXYLIC SYNTHETIC COMPLEX

REFERENCES CITED

Patent Documents

U.S. Pat. No. 4,007,290

Other Publications

Anderson D H, Mullins R F, Hageman G S, Johnson L V. 2002. A role for local inflammation in the formation of drusen in the aging eye. Am. J. Ophthalmol. 134(3): 411-431.

Anderson D H, Radeke M J, Gallo N B, Chapin E A, Johnson P T, Curlettie C R, Hancox L S, Hu J, Ebright J N, Malek G, Hauser M A, Rickman C B, Bok D, Hageman G S, Johnson L V. 2010. The pivotal role of the complement system in aging and age-related macular degeneration: hypothesis revisited. Prog. Ret. Eye Res. 29: 95-112.

Cushman M, Kanamathareddy S. 1990. Synthesis of the covalent hydrate of the incorrectly assumed structure of aurintricarboxylic acid. Tetrahedron 46(5): 1491-1498.

Cushman M, Kananathareddy S, De Clercq E, Scols D, Goldman M E, Bowen J A. 1991. Synthesis and anti-HIV activities of low molecular weight aurintricarboxylic acid fragments and related compounds. J. Med. Chem 34: 337-342.

Cushman M, Wang P, Stowell J G, Schols D, De Clercq E. 1992. Structural investigation and anti-HIV activities of high molecular weight ATA polymers. J. Org. Chem. 57: 7241-7248.

Gonzalez R G, Blackburn B J, Schleich T. 1979. Fractionation and structural elucidation of the active components of aurintricarboxylic acid, a potent inhibitor of protein nucleic acid interactions. Biochimica et Biophysica Acta 562: 534-545.

Heisig G B, Lauer M. 1941. Ammonium salt of aurin tricarboxylic acid. Organic Syntheses 1: 54.

Kira S, Ihara K, Takada H, Gondo K, Hara T. 1998. Nonsense mutation in exon 4 of human complement C9 gene is the major cause of Japanese complement C9 deficiency. Human Gen. 102(6): 605-610.

Lee M, Schwab C, McGeer P L. 2011. Astrocytes are GABAergic cells that modulate microglial activity. Glia 59: 152-165.

McGeer P L, Akiyama H, Itagaki S, McGeer E G. 1989. Activation of the classical complement pathway in brain tissue of Alzheimer patients. Neuroscience Letters 107: 341-346

Owens M R, Holme S. 1996. Aurin tricarboxylic acid inhibits adhesion of platelets to subendothelium. Thrombosis Res. 81: 177-185.

Rogers J, Cooper N R, Webster S, Schultz J, McGeer P L, Styren S D, Civin W H, Brachova L, Wang P, Kozlowski J, Cushman M. 1992. Isolation and structural elucidation of low molecular weight components of aurintricarboxylic acid (ATA). J. Org. Chem. 57: 3861-3866.

Yasojima K, Schwab C, McGeer E G, McGeer P L. 2001. Generation of C-reactive protein and complement components in atherosclerotic plaques. American J. Pthol. 158(3): 1039-1051.

FIELD OF THE INVENTION

This invention pertains to the use of low molecular weight components of the aurin tricarboxylic acid synthetic complex and their derivatives, to treat human conditions where self damage is caused by the membrane attack complex of complement

BACKGROUND OF THE INVENTION

Numerous agents have been described which will inhibit the complement system. These include heparin, suramin, epsilon-aminocaproic acid, and tranexamic acid. However, no orally effective agents have been described that will leave the necessary opsonization by complement functional, but which will prevent self damage by blocking assembly of the membrane attack complex. Eculizumab, a parenterally effective humanized monoclonal antibody which blocks C5 conversion has been described, but, as a high MW immunoglobulin antibody, it will not cross the blood brain barrier and will not be effective in CNS disorders. We show in this invention that components of less than 1 kDa MW of the aurin tricarboxylic acid synthetic complex (ATAC) blocks MAC assembly at the final stage of C9 addition and that they are safe and effective following oral administration.

Complement is a key component of both the innate and adaptive immune systems. It carries out four major functions: recognition of a target for disposal, opsonization to assist phagocytosis, generation of anaphylatoxins, and direct killing of cells by insertion of the membrane attack complex (MAC) into viable cell surfaces. Although complement is an essential defense system of living organisms, it is widely regarded as a two edged sword. Its opsonizing components are beneficial, but the membrane attack complex is potentially self damaging.

The complement system as it is understood today is illustrated in FIG. 1. It consists of two main pathways: the classical and the alternative. The pathways have differing opsonizing mechanisms, but they have in common assembly of the terminal components to form the membrane attack complex (C5b-9). The classical pathway commences with the C1q component of the C1 complex recognizing a target that needs to be phagocytosed. Subsequent steps involve dissociation of the C1 complex, cleavage of C2, C4, and C3 to provide amplification as well as covalent attachment of the activated complement components to the target. By this means the target is disposed of by phagocytes that have receptors for the activated complement components so attached.

Both pathways result in C5 being cleaved into C5a and C5b. The released C5b fragment can then insert itself into the membranes of nearby cells. C6, C7, C8 and C9 (n) can then become sequentially attached to the membranes. The addition of C9 renders the complex functional by opening holes in the membranes, thus leading to death of the cells. Its physiological purpose is to kill foreign pathogens, but in the case of sterile lesions, it can destroy host cells by the phenomenon known as bystander lysis.

The complement system therefore operates in two parts. The first part is opsonization, which prepares targeted tissue for phagocytosis. The second part is assembly of the membrane attack complex, which has the purpose of killing cells. The former is essential, but the latter is not. For example, approximately 0.12% of Japanese are homozygous for the nonsense CGA-TGA (arginine 95stop) mutation in exon 4 of C9 (Kira et al., 1999). These individuals cannot make a functioning membrane attack complex. This means that there are more than 150,000 Japanese leading healthy lives despite this deficiency. The Japanese experience indicates that selective inhibition of membrane attack complex formation on a long term basis is a viable therapeutic strategy.

The membrane attack complex exacerbates the pathology in all diseases where there is persistent overactivity of the complement system. Such diseases include, but are not limited to, age related macular degeneration, Alzheimer's disease, and atherosclerosis. This purpose of this invention is to provide a method for successfully treating such conditions by eliminating the danger of bystander lysis caused by the membrane attack complex of complement. This is achieved through administration of low molecular weight component of the aurin tricarboxylic acid synthetic complex which include aurin tricarboxylic acid (ATA), aurin quadracarboxylic acid (AQA), aurin hexacarboxylic acid (AHA), and their combination termed ATAC.

SUMMARY OF THE INVENTION

This invention is based on properties of components of the aurin tricarboxylic acid synthetic complex of less than 1 kDa (ATAC). For many years it was assumed that the product obtained by the classical aurin tricarboxylic acid synthetic method, originally described by Heisig and Lauer in 1929 (Heisig and Lauer, 1941), consisted only of aurin tricarboxylic acid itself (e.g. U.S. Pat. No. 4,007,270). It has been extensively documented since issuance of that patent that this standard procedure, and variations of it, produce a complex of compounds, the majority of which are of high molecular weight of still uncertain structure (Cushman and Kanamathareddy, 1990; Gonzalez et al., 1979). These high molecular weight components bind preferentially with proteins (Cushman et al., 1991), especially those interacting with nucleic acids (Gonzalez et al., 1979). This invention circumvents these problems by utilizing molecular weight components of the aurin tricarboxylic acid complex of less than 1 kDa which act at low concentrations as selective blockers of the membrane attack complex of complement.

This invention can be utilized for the treatment of all human conditions where there is chronic activation of the complement system and where it has been shown by autopsy studies that the membrane attack complex exacerbates the lesions. These conditions include, but are not limited to, Alzheimer disease, age related macular degeneration, and atherosclerosis.

In 1977, U.S. Pat. No. 4,007,270 was issued for "Complement Inhibitors" which included aurin tricarboxylic acid but which did not show, or specify, that the inhibitors, to be useful needed to be selective for the membrane attack complex. Those skilled in the art would have concluded that aurin tricarboxylic acid, as described in that patent, is not a specific inhibitor of the membrane attack complex, and would not be useful in the applications described in this invention. Firstly, they would have been taught, on the basis of molecular analyses conducted subsequently to issuance of U.S. Pat. No. 4,007,270, that the product, as produced by the synthetic method described in the patent, would not be aurin tricarboxylic acid, but would consist mostly of a mixture of high molecular weight materials of uncertain structure (e.g. Gonzalez et al., 1978, Kushman and Kanamatharedy, 1990). They would further have been taught that these components have powerful side effects which would render them unsuitable for human administration, including inhibition of protein nucleic acid interactions (Gonzales et al., 1979), and inhibition of adhesion of platelets to endothelium (Owens and Holme, 1996). They would also have been taught that the mechanism of action was against the opsonizing components of complement as shown by the described effects on C1 inhibitor (Test Code 026) and not be selective inhibition of the membrane attack complex. Therefore, by inhibiting the essential function of opsonization, it would be unsuitable for chronic administration. Finally, they would have concluded it would be of no use in disorders such as Alzheimer's disease, age related macular degeneration, and atherosclerosis since these are not diseases of humoral origin as described in the patent. In summary, there has been extensive teaching away from our invention and those skilled in the art would have been motivated against pursuing it.

The material for this invention can be obtained by starting with the product of synthesis using the method of Cushman and Kanamathareddy (Cushman and Kanamathareddy, 1990). It can also be prepared from commercial sources, particularly the triammonium salt of the aurin tricarboxylic acid complex known as Aluminon.

More than 85% of the synthesized powder, or equivalent powder obtained from commercial sources including Aluminon, is a mixture of high molecular weight polymeric products. The exact structures of these products are as yet uncertain (Gonzales et al., 1979; Cushman and Kanarmathareddy, 1990; Wang et al., 1992; Cushman et al., 1992).

Figure 2A:
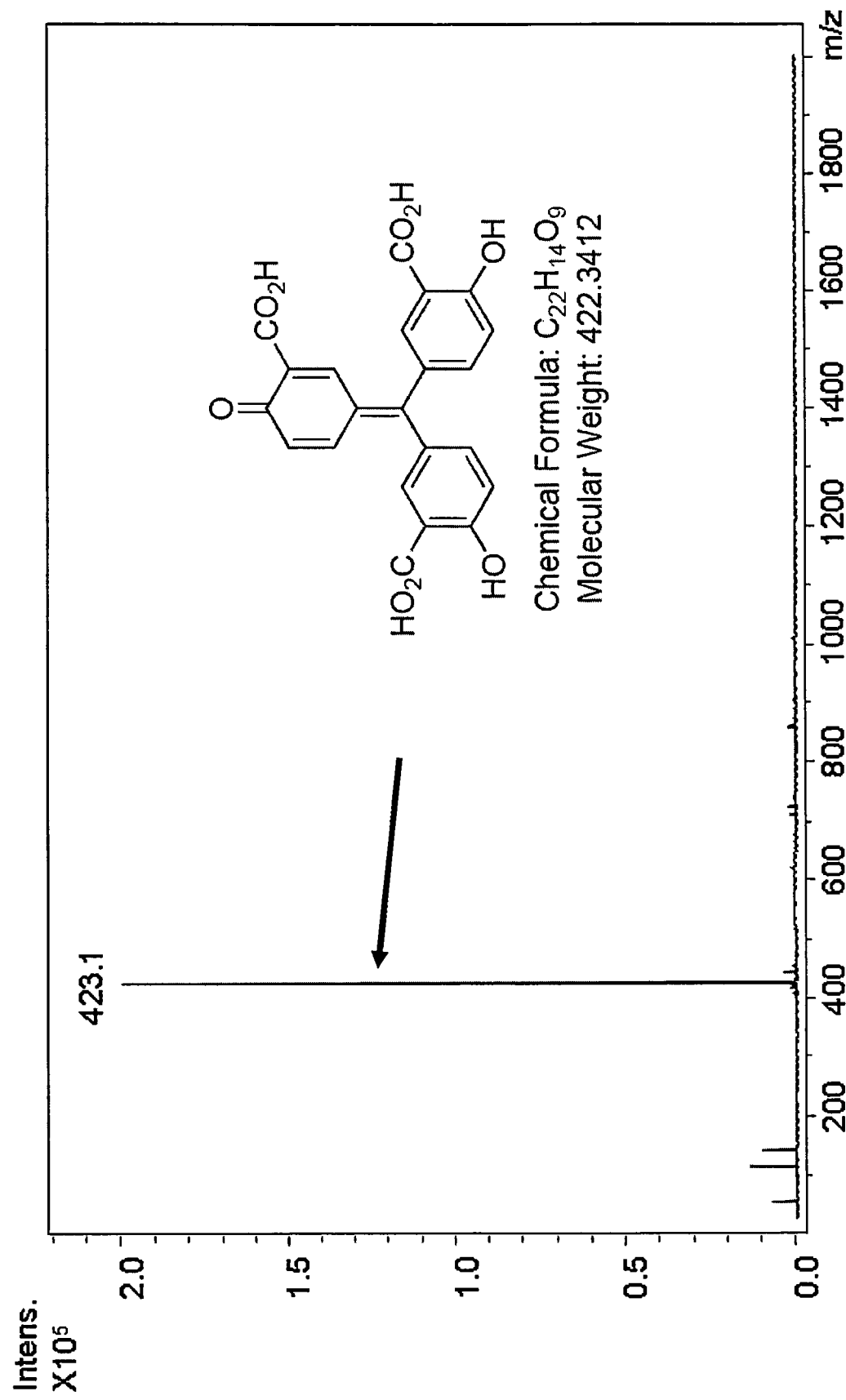
Figure 2B:
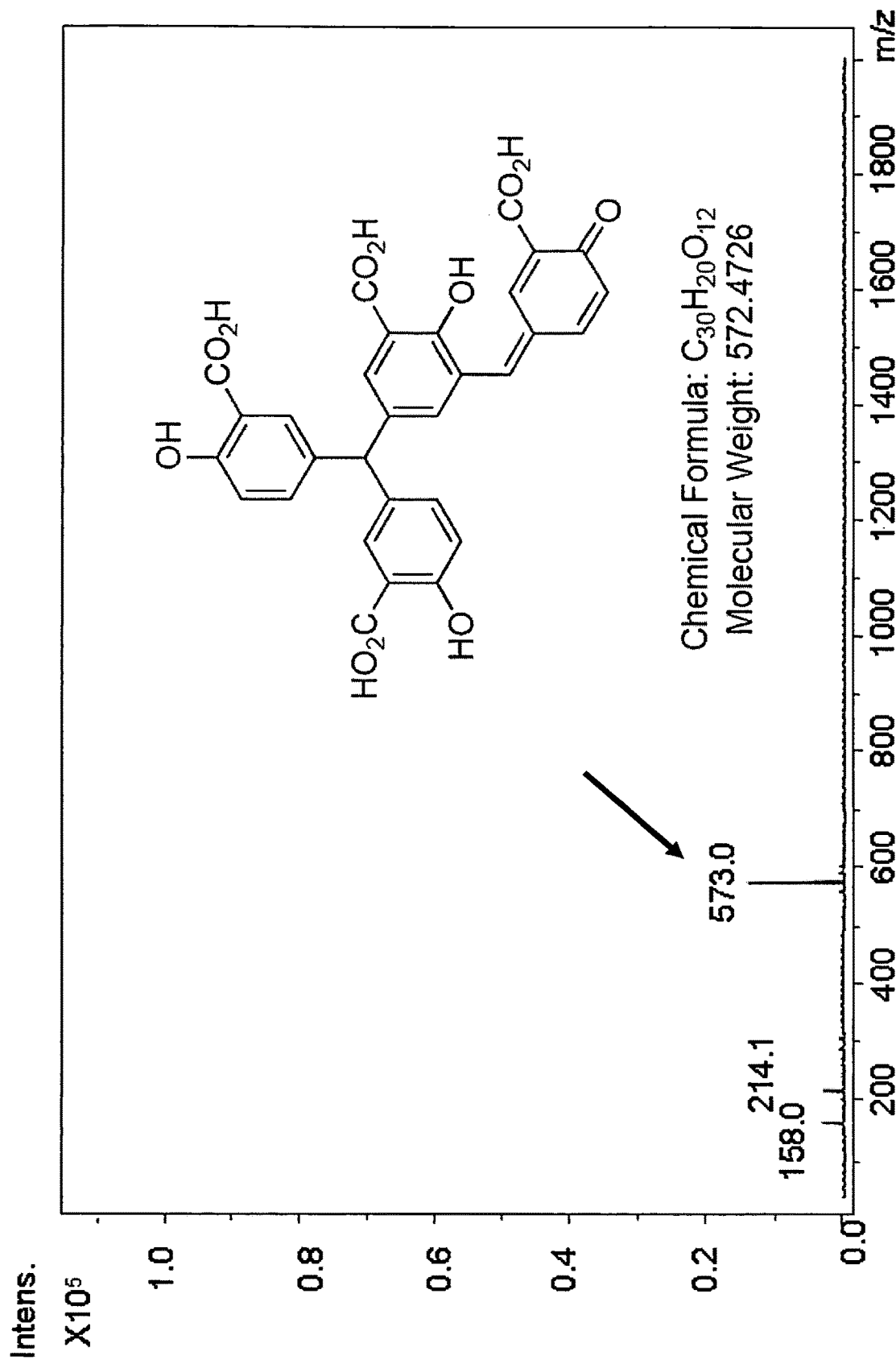
Figure 2C:
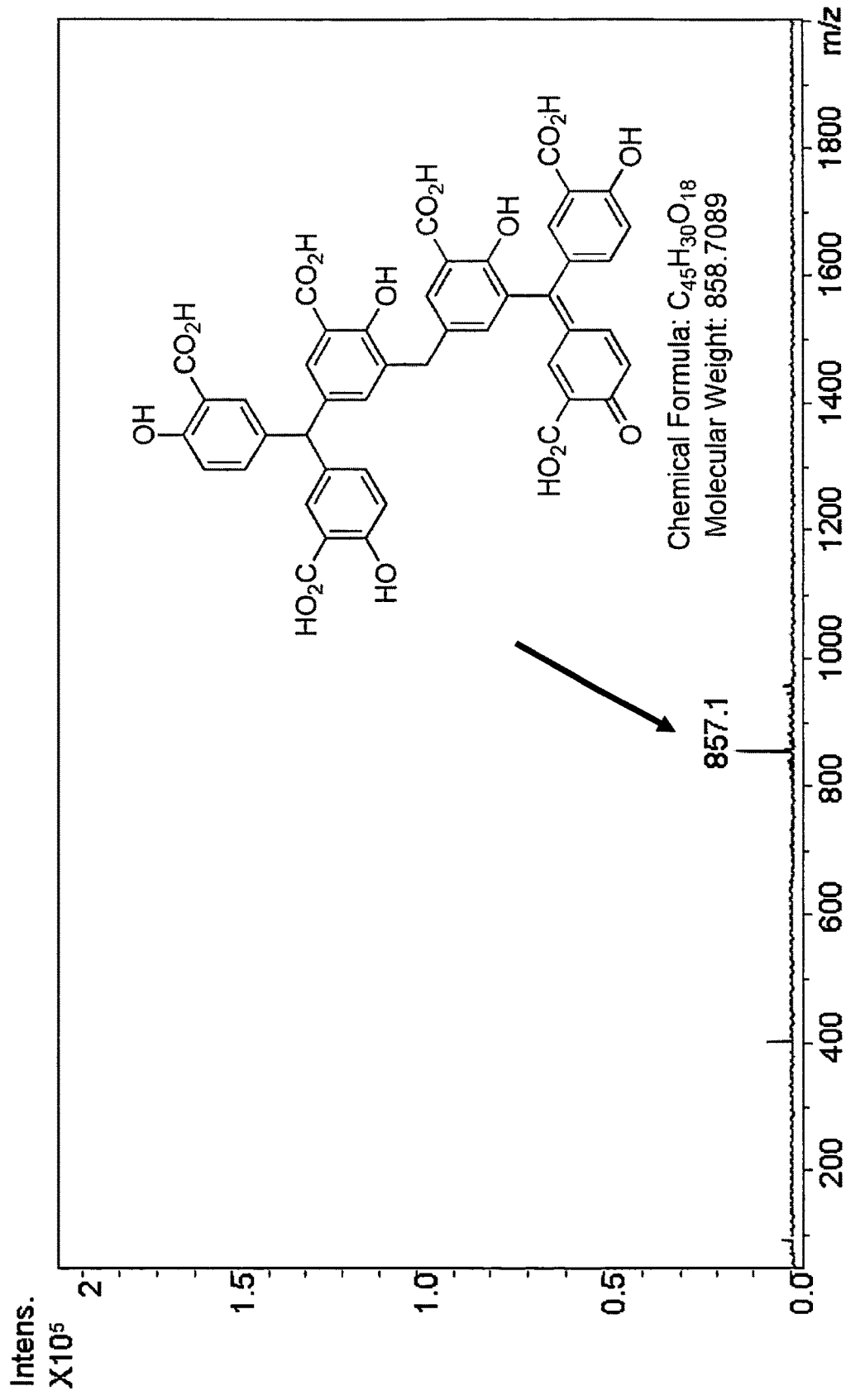

The powder obtained from synthesis or from commercially purchased Aluminon were separated into high and low molecular weight components by passing through 1 kDa and 0.5 kDa MW filters. The low MW components were separated and analyzed by mass spectroscopy. Results from the two sources were almost identical. The low MW components made up only 16% of the total. The low molecular weight component contained three molecules of MW 422, 572, and 858. These MWs correspond to structures with three, four and six salicylic acid moieties. We refer to these as aurin tricarboxylic acid (ATA), aurin quadracarboxylic acid (AQA) and aurin hexacarboxylic acid (AHA) (FIG. 2). They were in the proportion of 78% ATA, 15% AQA and 7% AHA. This mixture is referred to as the aurin tricarboxylic acid complex (ATAC).

We show in this invention that AHA, AQA, ATA and ATAC selectively block the addition of C9 to C5b-8 so that the MAC cannot form. These molecules inhibit hemolysis of human, rat, and mouse red cells with an $IC_{50}$ in the nanomolar range. When given orally to Alzheimer disease type B6SJL-Tg mice, they inhibit MAC formation in serum and improve memory retention. On autopsy, they show no evidence of harm to any organ. We conclude that this invention may be effective in the therapy of a spectrum of human disorders where self damage from the MAC occurs.

DRAWINGS: IN THE DRAWINGS

FIG. 1. Shows a schematic representation of the classical complement pathway as activated in Alzheimer disease, and the alternative complement pathway as activated in age related macular degeneration. Notice that assembly of the membrane attack complex is common to both the classical and alternative pathways.

FIG. 2. Shows the putative structure and mass of the three components of the aurin tricaboxylic acid synthetic complex (ATAC) of less than 1 KDa and corresponding mass-spec analyses. (a) ATA, MW 422 (5,5'-((3-carboxy-4-oxocyclohexa-2,5-dienn-1-ylidene)methylene)bis(2-hydroxybenzoic acid) (b) AQA, MW 572 (putative structure 5,5-((3-carboxy-5-((3carboxy-4oxocyclohexa-2,5-dien-1-ylidene)methyl)-4-hydroxyphenyl)methylene)bis(2hydroxybenzoic acid)) (c) AHA, MW858 (putative structure, 5,5'-((3-carboxy-5-((3- carboxy-4-oxocyclohexa-2,5-dien-1-ylidene)methyl)-4-hydroxybenzyl)-4-hydroxyphenyl)methylene)bis(2-hydroxybenzoic acid)). ES– means negative scan mode, giving values of –1 to the true mass. ES+ mean positive scan mode giving values of +1 to the true mass.

Figure 3A:
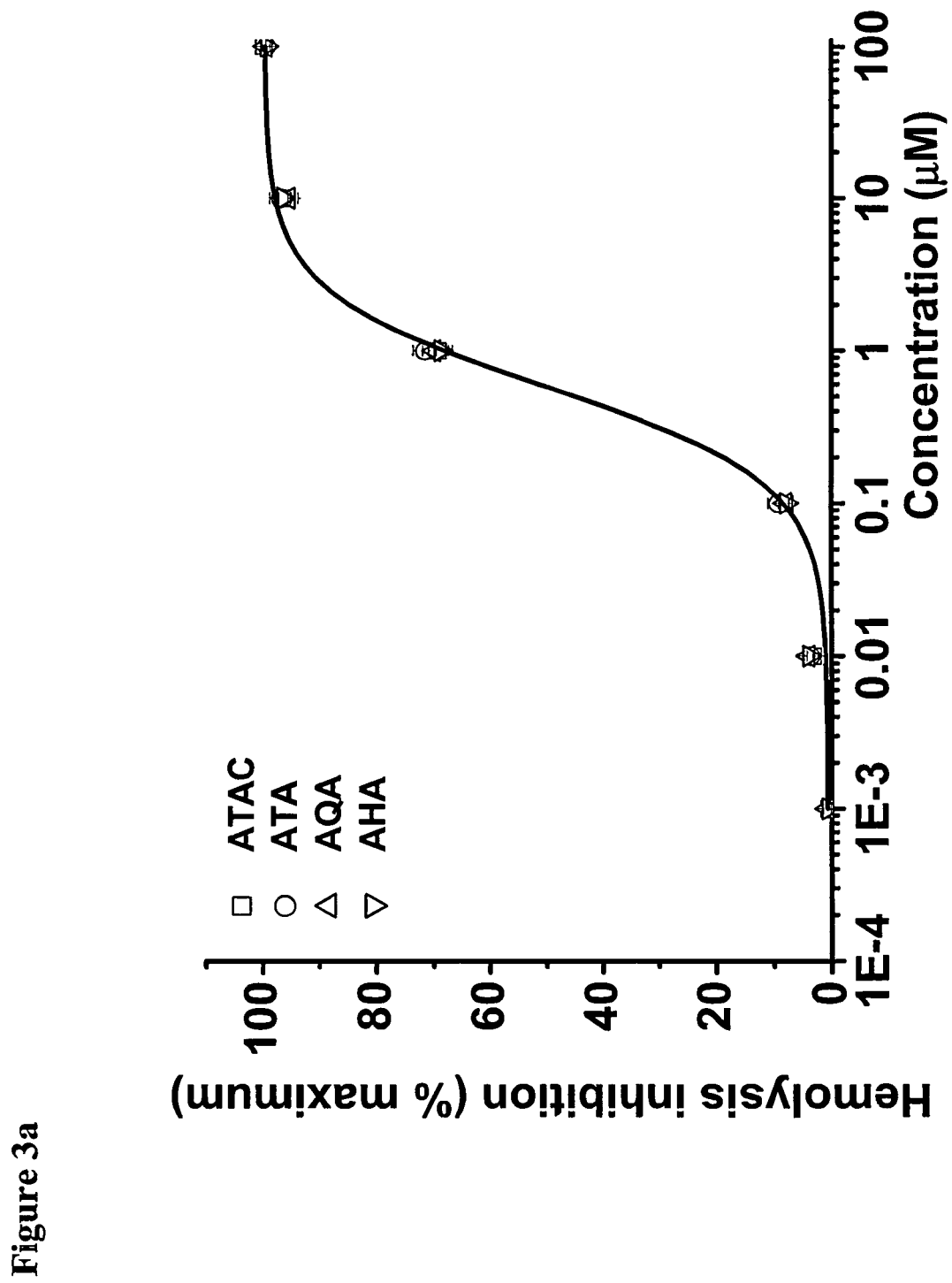
Figure 3B:
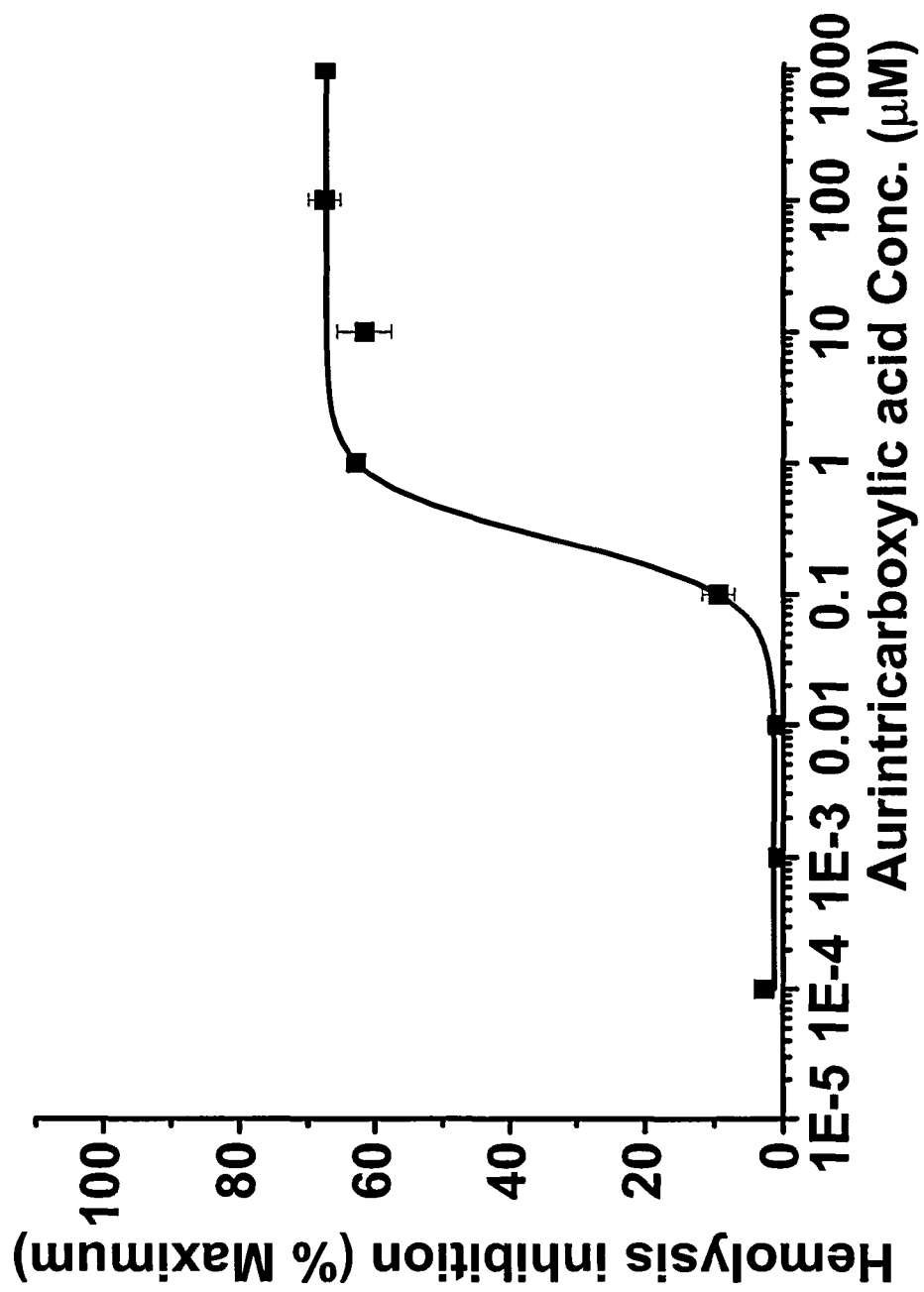

FIG. 3. Shows the CHSO analyses of human and rat serum. Notice the almost identical $IC_{50}$ values of each component. They were (nM) for ATA 544, for AQA 576, for AHA 559 and for ATAC 580. The $IC_{50}$ for ATAC in rat serum was 268 nM.

FIG. 4. Shows Western blot analyses demonstrating that ATA, AQA, AHA, and ATAC act selectively by blocking the addition of C9 to C5b678 thus preventing formation of the membrane attack complex. Normal human serum was pre treated with aliquots of aqueous solutions of ATA, AQA, AHA and ATAC prior to adding sheep red blood cells sensitized to human complement. The reaction mixtures were incubated at 37° C. for 1 h. Aliquots were loaded on 10% polyacrilamide gels and subjected to SDS-PAGE. Proteins were transferred to membranes and developed with appropriate primary antibodies to complement proteins (Table 1): (a) Western blots of membranes developed with antibodies to C1q, C3, C4 and C5. Lane 1, untreated serum; lane 2, serum with red blood cells added; lane 3 serum protected with ATAC and red blood cells. Notice that in untreated serum bands for C1q, C3, C4, and C5 were readily detected. In lanes 2 and 3 the activated products C3d, C4d, and C5a were detected indicating opsonization had taken place. In lane 3, the MAC was detected, but not in lane 4, indicating that ATAC was blocking MAC formation. To analyze which step in MAC formation was involved, Western blot membranes were treated with antibodies to C6, C7, C8, and C9 for (b) ATAC, (c) ATA, (d) AQA and (e) AHA. The results are identical. In each panel, lane 1 is serum, lane 2 is unprotected red blood cells, lane 3 is protected red blood cells, and lane 4 is the same as lane 3 but with C9 protein supplementation. It shows that C6, C7, C8 and C9 are readily detected in untreated serum. Lane 2 shows that, in unprotected red blood cells that have become hemolysed by complement attack, only C5b-9, the fully formed membrane attack complex, is detected. Lane 3, in which the cells have been protected either by ATA, AQA, AHA or ATAC, the membrane attack complex does not fully form but becomes arrested at the C8 stage. The C6 antibody detects C5b6, C5b67, and C5b678. The C7 antibody detects C5b67 and C5b678, while the C8 antibody detects C5b678. Lane 4 provides confirmation that the blockade occurs only at the C9 stage. It can be seen that C5b-9 is now detected upon probing with C6, C7, C8 and C9, thus establishing that the ATAC block was at the C9 stage. A very faint C9 band is still visible in the blots indicating that not all the added C9 was consumed in the process.

Figure 5:
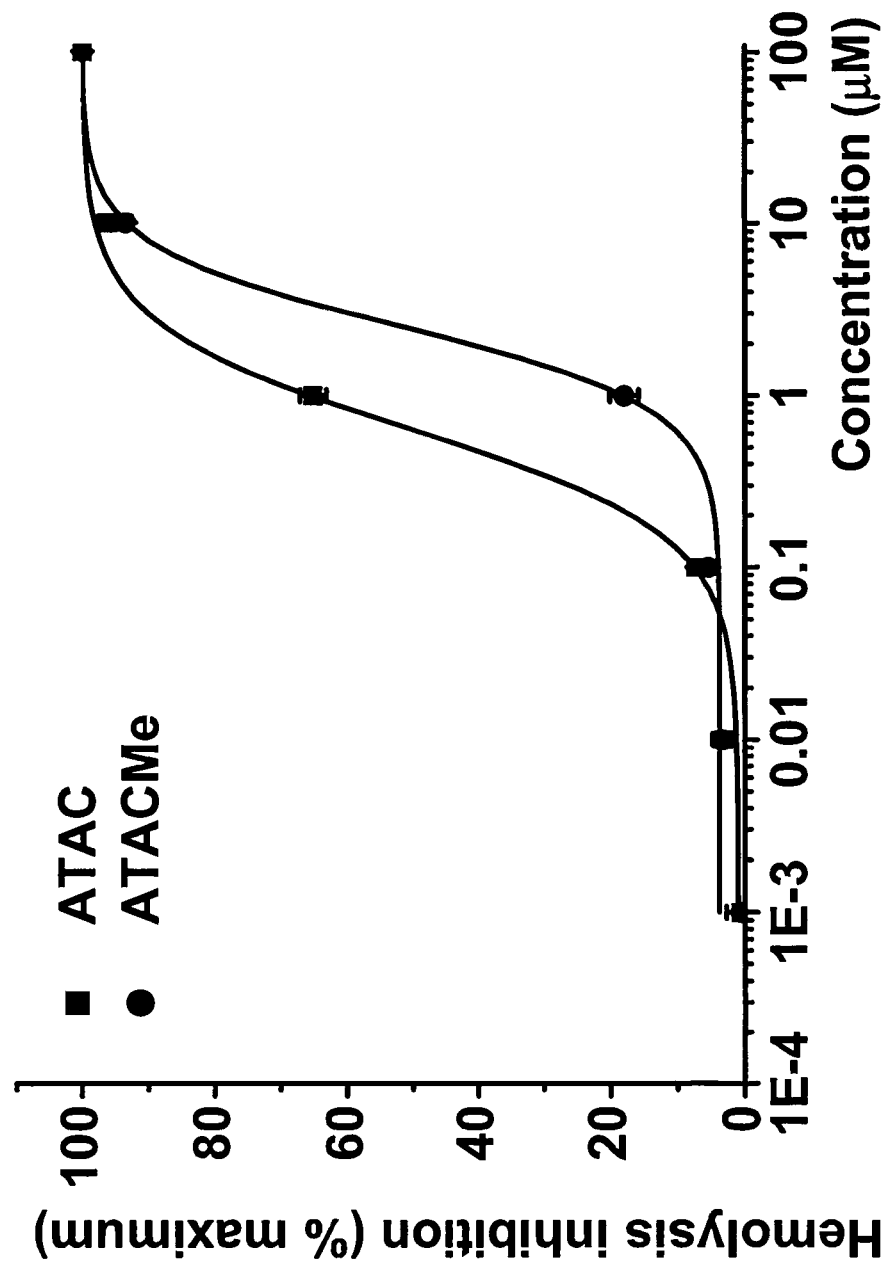

FIG. 5. Shows a comparison of CHSO results in human serum of ATAC and the methyl derivatives of ATAC. The methyl derivatives were less effective than ATA with an estimated $IC_{50}$ of 2.52 µM.

Figure 6:
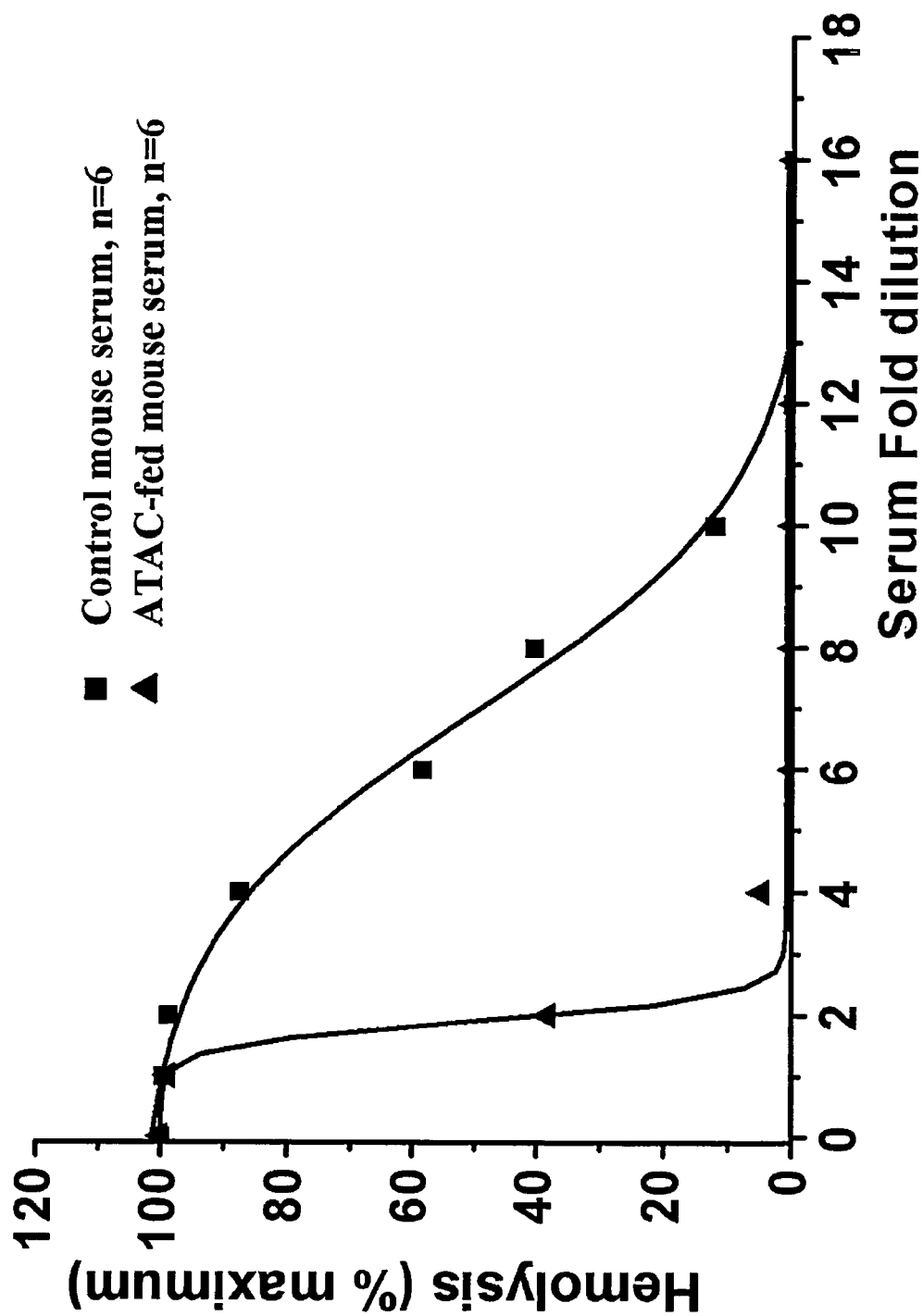

FIG. 6. Shows the effects of orally administered ATAC on complement activation of mouse serum. Serum from six B6SJL-Tg mice fed normal chow was combined and compared with the combined serum from six B6SJL-Tg mice fed ATAC supplemented chow. The sera were subjected to 1-16 fold dilutions. The solutions (25 microliters) were incubated with 100 microliters of antibody-conjugated sheep red blood cells ($5 \times 10^6$ cells) for 1 h. The mixtures were centrifuged, and the relative amount of hemoglobin released into 100 microliters of supernatant recorded by the absorbance at 405 nanometers. Serum from mice fed normal chow required more dilution than ATAC-fed mice for hemolysis to occur. The $IC_{50}$s were 6.89 and 1.92 fold respectively corresponding to a 3.59 fold protection.

Figure 7:
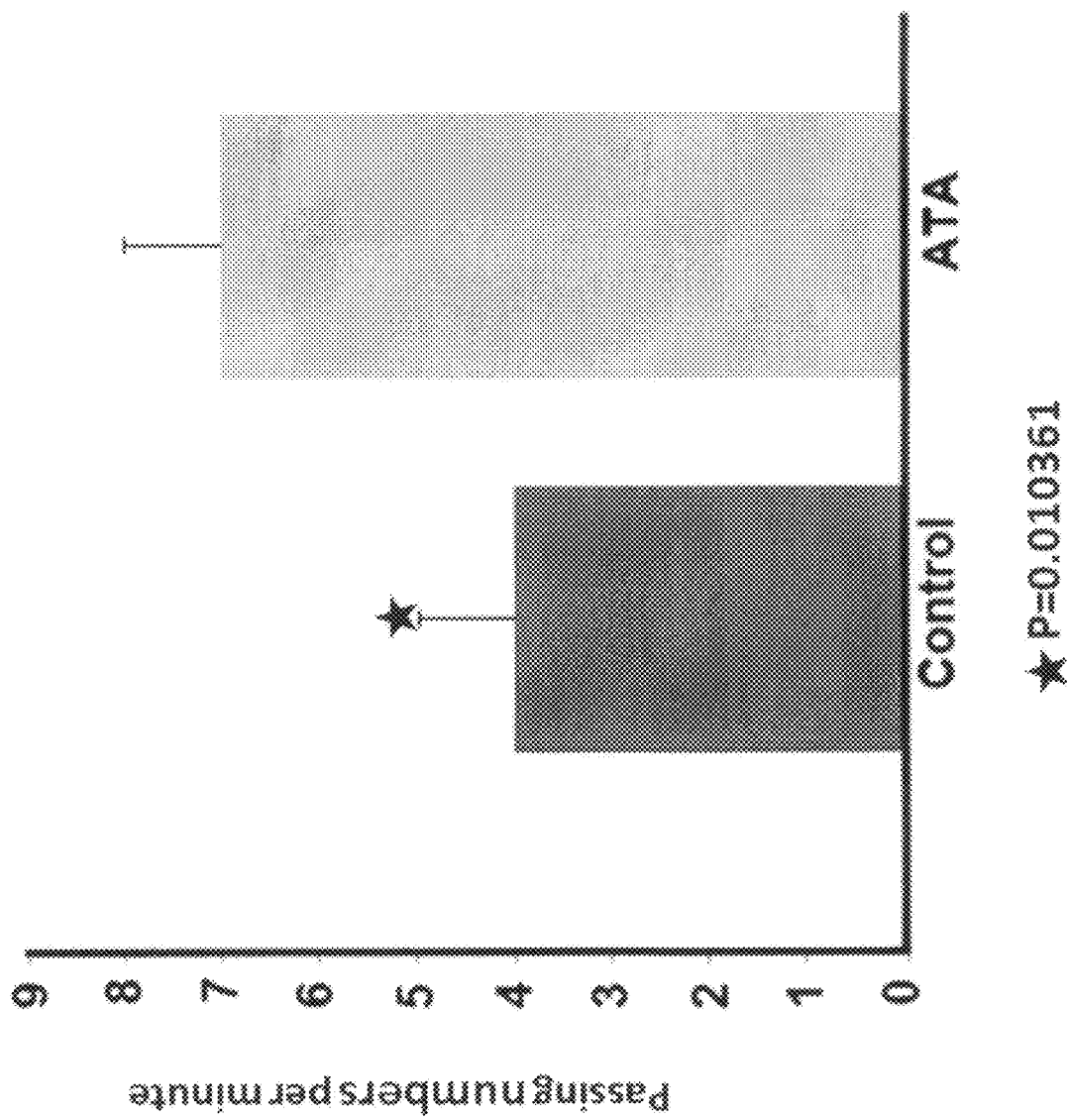

FIG. 7. Shows memory retention of ATAC fed B6SJL-Tg mice compared with normal chow fed B6SJL-Tg mice as assessed by the rate of searching in the vicinity of the hidden platform after its removal on day 6 of testing. ATAC fed mice showed a significantly greater time searching in the correct area of the missing platform than mice fed normal chow, indicating a better retention of memory.

Table 1. Lists the antibodies used to detect complement proteins in Western blots

DETAILED DESCRIPTION OF A PREFERRED EMBODIMENT OF THE INVENTION

Synthesis of the Aurin Tricarboxylic Acid Complex

Synthesis of the aurin tricarboxylic acid complex was carried out with slight modifications of the previously published standard procedure (Cushman and Kanamathareddy, 1990).

1. Synthesis of 3,3'-dichloro-5,5'-dicarboxy-4,4'-dihydroxydiphenylmethane

3-Chlorosalicylic acid (1 g) was dissolved in methanol (10 ml). Water (2.5 ml) was added and the flask was cooled to –5° C. in an ice-salt (NaCl) bath. Concentrated sulfuric acid (30 ml) was slowly added over 20 min with the temperature being maintained at –5° C. The reaction mixture was then stirred at this temperature for 1 h while a solution of 37% formaldehyde (4 ml) was added. The temperature was maintained at 0° C. for 1 h and then the mixture was left at room temperature for a further 24 h. The reaction mixture was poured into crushed ice (150 g) and the precipitate filtered and dried to give the product, 3,3'-dichloro-5,5'-dicarboxy-4,4'-dihydroxydiphenylmethane (yield 0.92 g, 92%) as a powder. The sample was recrystallized from methanol.

2. Synthesis of 3,3'-dicarboxy-4,4'-dlhydroxydiphenylmethane 3,3'-Dichloro-5,5'-dicarboxy-4,4'-dihydroxydiphenylmethane (0.92 g) was dissolved in ethanol (18 ml) and triethylamine (10 ml). Pallidiun on carbon was added to the solution and the mixture was stirred under an atmosphere of hydrogen for 48 h. The catalyst was filtered off, the solvent evaporated, and water (100 ml) added to the residue. The solution was cooled, and concentrated hydrochloric acid (5 ml) added. The white precipitate was filtered and dried to give the product, 3,3'-dicarboxy-4,4'-dihydroxydiphenylmethane (0.75 g, 90%) as a solid. It was dissolved and recrystallized from methanol.

3. 3,3',3"-tricarboxy-4,4',4"-trihydroxytriphenylcarbinol complex (aurin tricarboxylic acid complex)

Powdered sodium nitrite (4 g) was added with vigorous stirring to concentrated sulfuric acid (4 ml). A mixture of the compound 3,3'-Dicarboxy-4,4'-dihydroxydiphenylmethane (0.75 g) and salicylic acid (0.38 g) was stirred until it was homogeneous. It was then poured into the solution of sodium nitrite-sulfuric acid. Stirring was continued at room temperature for an additional 18 h. The mixture was poured into crushed ice (100 g) with stirring. The dark orange precipitate was filtered and dried to give the product, aurin tricarboxylic acid complex (0.6 g, yield 60%). The powder was dissolved in 2% ammonium hydroxide for analysis.

Separation and Analysis of ATAC

The ammonium salt of the crude aurin tricarboxylic acid synthetic complex (Aluminon) was purchased from the GFS Chemicals Inc. (Columbus, Ohio). Five grams of material was dissolved in 0.2% ammonium hydroxide (45 ml) and forced through a 1 kDa filter (PLAC04310, Millipore, Ballerica, Mass.) under air pressure (70-75 Psi, 5.3 kg/cm$^2$ for 6 h). The filtered ATAC was recrystallized by lyophilization. The filtrate (4.5 mg in 1 ml) was then loaded onto a size exclusion chromatography column (Sephadex LH-20 packed in 60% ethanol, GE healthcare, Piscataway, N.J.). Three different eluant fractions were collected. The three fractions, as well as the starting mixture, were analyzed by mass spectrometry on a Waters ZQ apparatus equipped with an ESCI ion source and a Waters Alliance Quadrupole detector. All samples were exposed to electron spray ionization in positive and negative modes, as well as atmospheric pressure chemical ionization. Scans ranged from m/z 0-1100 and m/z 500-1500. Three molecules were detected of MW 422, 572, and 858. These molecular weights correspond to ATA, AQA, and AHA respectively as shown in FIG. 3. There was no other derivative of less than 1.5 kDa detected.

Evaluation of the Low Molecular Weight Products as Selective Inhibitors of the Membrane Attack Complex To evaluate the strength of blockade of the classical complement pathway by the low molecular weight products of the aurin tricarboxylic acid complex, (i.e. ATA plus AQA plus AHA), the standard CHSO assay was employed. Sheep red blood cells were sensitized by incubation overnight with rabbit anti sheep red blood cell antibody. Then dilutions of serum, with and without various amounts of the low molecular weight aurin tricarboxylic acid fraction (ATAC), were incubated with the sensitized red blood cells for 1 hour at 37° C. The incubates were centrifuged at 5,000 rpm for 10 min. The hemoglobin released into the serum from red blood cells that had been destroyed by complement attack, was determined by reading the optical density (OD) at 405 nm. As a positive control, red blood cells were 100% lysed with water, and as a negative control, no serum was added to the incubate.

The results are shown in FIG. 4. Each of these components inhibited human complement-mediated red blood cell hemolysis almost identically. IC$_{50}$ values were for ATA 544 nM, for AQA 576 nM, for AHA 559 nM and for ATAC 580 nM. The IC$_{50}$ for ATAC in rat serum was 268 nM. These data establish that inhibition of complement activation by low molecular weight aurin tricarboxylic acid derivatives is in the nanomolar range and includes rodent as well as human serum To determine at which stage of the complement cascade blockade was occurring, a variation of the CH50 assay was carried out. Instead of measuring hemolysis, Western blot analyses were run to determine which serum complement proteins were consumed and converted into activated complement products. Serum proteins are consumed and converted only up to the stage of blockade. At stages beyond the blockade, they remain unchanged in the serum. Results are shown in FIG. 5. Human serum was diluted 16 fold. It was then treated for 30 min with either ATA, AQA, AHA or ATAC. Then antibody-conjugated sheep red blood cells in an equal volume were added. The mixtures were incubated at 37° C. for 1 h. They were then treated with a lysis buffer followed by a loading buffer for Western blots. Equal amounts of protein from each sample were loaded onto gels and separated by 10% SDS-PAGE. Following SDS-PAGE, proteins were transferred to a PVDF membrane. The membranes were then treated with various primary antibodies followed by labeled secondary antibodies using well established techniques (Lee et al., 2011). The list of antibodies that were utilized is shown in Table 1. Bands recognized by the antibodies were visualized by use of an enhanced chemiluminescence system and exposure to photographic film. For probing the same membrane with different antibodies, the membranes were treated with stripping buffer (Lee et al., 2011) and then treated as before with a different primary antibody.

Figure 4A:
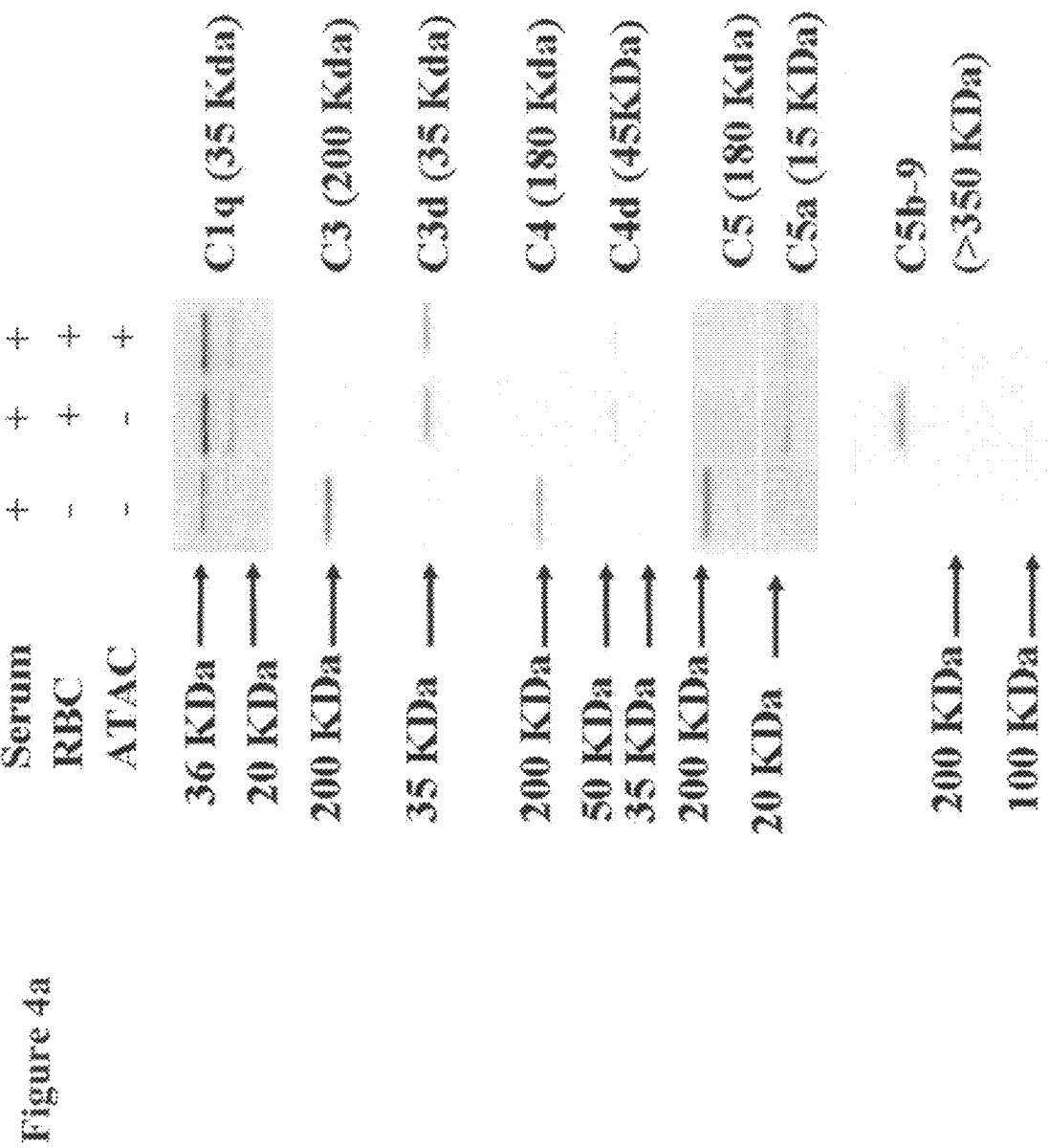

Typical results are shown in FIG. 4a. The left lane was loaded with serum only and shows that bands for C1q, C3, C4, and C5 were readily detected. The adjacent lane illustrates the effect of adding sensitized red blood cells, which then become hemolized by complement attack. Native serum proteins are consumed and become incorporated into the red cell membranes. C1q was unmetabolized, but the band was intensified due to its dissociation from the C1 complex. Native C3 was no longer detected because it had been cleaved, and the C3b fragment had become covalently attached to the membrane. The degradation product C3d was detected. C4 was no longer detected because it had similarly been cleaved and the C4b fragment attached to the membrane and metabolized into the degradation product C4d. This fragment was also detected. C5 was cleaved and a band for the C5a product detected. Finally, the C5b-9 membrane attack complex, which had formed on the red cell membrane causing its hemolysis, was detected.

The next membrane shows the effect of incubation of serum plus sensitized red blood cells in the presence of the ATAC. Identical bands for the opsonization steps were detected, but the red cells were not hemolyzed and the membrane attack complex was not detected.

Figure 4B:
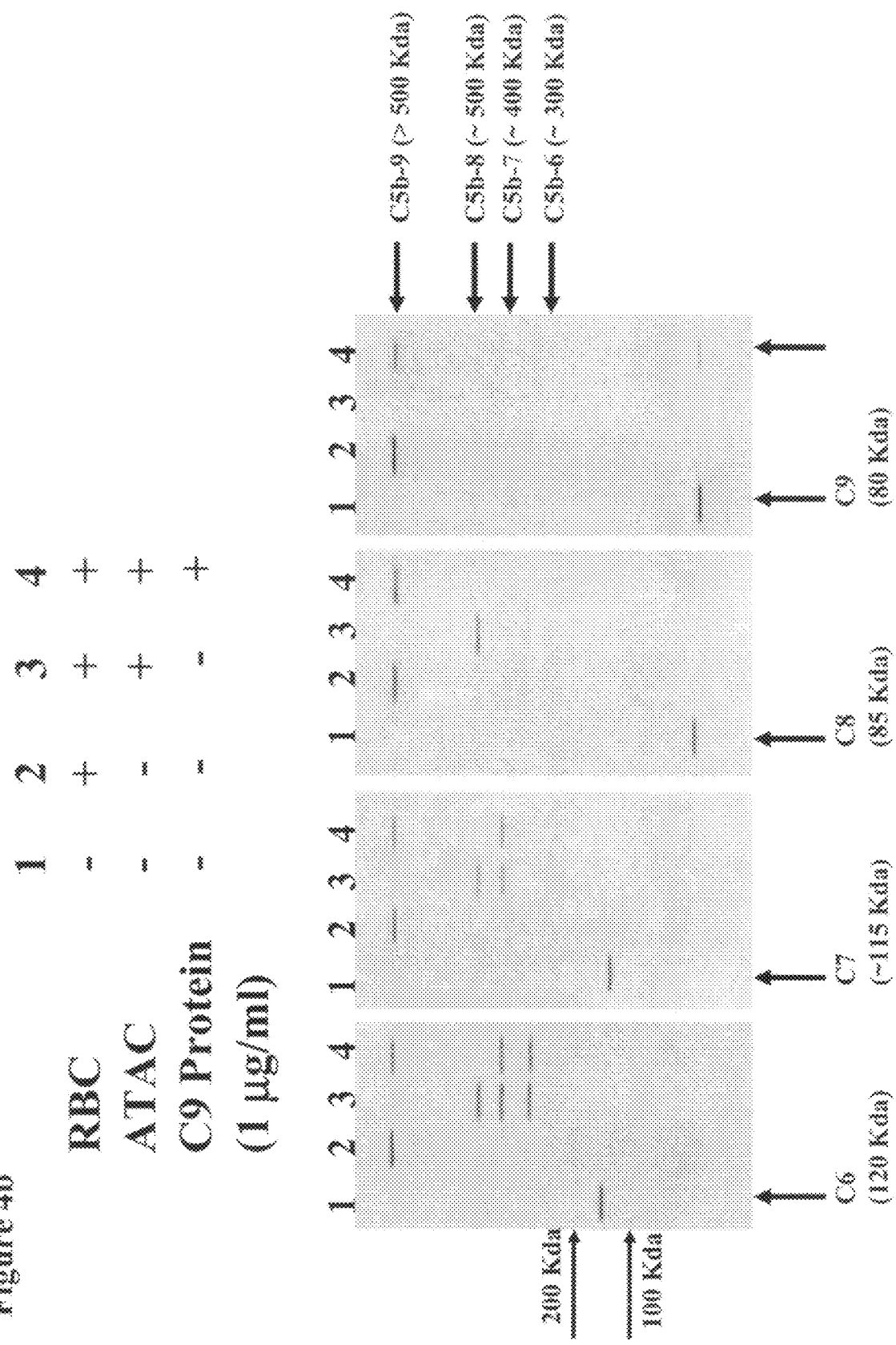

To determine at which stage of assembly of the membrane attack complex was being blocked, additional analyses were carried. The incubations were the same as before except that the red blood cells were separated from the residual serum and washed prior to being treated for Western blot analysis. The blots were probed with antibodies to C6, C7, C8 and C9. The results are shown in FIG. 4b for ATAC, 4c for AHA, for 4d for AQA and 4e for AHA. The results were identical for each component. Lane 1 for human serum alone shows that C6, C7, C8 and C9 were readily detected in the untreated serum. Lane 2 shows that in unprotected red blood cells that have become hemolyzed by complement attack, these antibodies detected only C5b-9, the fully formed membrane attack complex. Lane 3, in which the cells have been protected by ATAC, shows that the membrane attack complex does not fully form but becomes arrested at the C8 stage. The C6 antibody detected C5b6, C5b67, and C5b678. The C7 antibody detected C5b67 and C5b678, while the C8 antibody detected C5b678. These data establish that ATAC arrests formation of the membrane attack complex at the stage where C9 attaches to C5b678. Since C9(n) is required for creating the membrane destroying holes, this blockade is highly specific to preventing C9 attachment.

Synthesis and Filtration of ATA-Methylester

To illustrate that simple derivatives of ATAC also have complement inhibiting properties, the methyl ester was synthesized and tested by the CHSO assay on human serum.

The synthesis was carried out with a modification of the procedures previously published (U.S. Pat. No. 4,007,290). Briefly, ATAC (0.8 g) was dissolved in methanol (16 ml). Concentrated sulfuric acid (610 µl) was added. The reaction mixture was refluxed at 55° C. for 1 h. The solvent was evaporated and the remaining solid collected. The product was tested in a CHSO assay compared with the non-esterified material and was found to be 29% as active (FIG. 5, $IC_{50}$ 0.64 μM vs 2.52 μM assuming a MW of 422).

In Vivo Testing

Since the invention requires material that can be safely administered on a continuing basis, it requires testing in vivo in animals. This can be achieved by feeding to mice or other species, a mixture of the powder obtained added to their normal chow. Our example was with mice that are transgenic for Alzheimer disease mutations (B6SJL-Tg). By employing such mice, the product was tested not only for safety, but also for potential efficacy in Alzheimer disease.

Control B6SJL-Tg mice were fed normal chow, and test B6SJL-Tg mice were fed show supplemented with 0.5 mg/kg ATAC. Based on chow consumption, it was calculated that test mice were receiving 5 mg/kg/day of ATAC. Feeding was started at ages from 56-63 days and was continued for a further 30 days or 48 days before sacrifice. Upon autopsy, no evidence of pathology in any organ of either the ATAC fortified or normal chow fed mice was observed. These data indicate that ATAC is well tolerated and apparently safe when continuously consumed at a dose of 5 mg/kg/day for 44 days.

The results of CHSO assays are shown in FIG. 6. Serum at various dilutions (1-16 fold) was incubated with antibody-conjugated sheep red blood cells for 1 h. Serum from the fed mice required less dilution, consistent with inhibition of the membrane attack complex ($IC_{50}$ 1.92 fold vs. 6.89 fold for mice fed normal chow). These data indicate that a 3.59 fold protection was achieved. They establish that ATAC is absorbed after oral administration, and, at the doses tested, is an effective inhibitor of MAC formation.

B6SJL-Tg mice develop early memory deficits due to the rapid buildup of beta amyloid protein deposits. The memory of B6SJL-Tg mice fed normal or ATAC chow was tested using a standard water maze test. It was performed in a pool of 1.5 meter diameter with opaque fluid and a 10 cm diameter hidden platform. Mice were placed in the pool for first-day visible training, followed by four days of training where the platform was hidden. The next day they were measured with the hidden platform removed to determine how quickly they returned to where the hidden platform had been placed and thus how well they remembered its location. The tracking of animal movements in the area where the platform had been located was captured by an HVS2020 plus image analyzer. Data were analyzed by two-way ANOVA. It was found that ATAC treated mice performed 2.5 fold better than the untreated mice. The data are shown in FIG. 7. In summary, these in vivo data on Alzheimer disease transgenic mice show that ATAC is not only safe, but beneficial in these animals. It improves weight gain and memory retention, which correlates with its ability to inhibit formation of the membrane attack complex of complement.

Applicability of the Invention to the Treatment of Human Disease.

General considerations. The complement system has usually been interpreted as serving only the adaptive immune system. But it is also a mainstay of the innate immune system. It is called into play in all chronic degenerative diseases. If it is activated to the extent that the MAC is formed, there is danger of the pathology being exacerbated through bystander lysis. Therapeutic opportunities for intervention in a spectrum of human disease states have never been explored because there has never been previously described an orally effective complement inhibitor which is selective for blocking the MAC. The invention described here illustrates examples of diseases where benefit in common degenerative diseases can be expected from utilization the invention described here.

Alzheimer's disease. It has long been known that beta amyloid protein deposits in brain, which are believed to be the primary cause of the disease, can be identified by the opsonizing components of complement. It was demonstrated that this was due to C1q binding to beta amyloid protein (Rogers et al., 1992). It was also demonstrated that the membrane attack complex of complement decorated damaged neurites in the vicinity of the deposits, indicating self damage by the complement system (McGeer et al., 1989). Taken together, these data illustrate that the opsonizing aspects of complement need to be preserved so that phagocytosis of the beta amyloid deposits can occur, while the membrane attack complex needs to be selectively blocked so that self damage to host neurons can be eliminated.

Age related macular degeneration. Opsonizing components of complement have been identified in association with drusen, which are the extracellular deposits associated with the disease. The membrane attack complex has been found near the degenerating retinal pigment epithelial cells (Anderson et al., 2002). Genetic analyses have revealed that polymorphisms in Factor H, Complement Factor B, and C3 all significantly influence the risk of suffering from age related macular degeneration (Anderson et al., 2010). These data illustrate that the opsonizing aspects of complement need to be preserved so that phagocytosis of drusen can occur, while the membrane attack complex needs to be selectively blocked so that self damage to retinal pigment epitheleial cells can be eliminated.

Atherosclerosis. Atherosclerosis has not generally been considered to be exacerbated by the complement system. However the mRNA for C-reactive protein, a known activator of complement, is upregulated more than ten fold in the area of atherosclerotic plaques. Plaque areas showing upregulation of C-reactive protein and the opsonization components of complement also demonstrate presence of the membrane attack complex (Yasojima et al., 2001). This is a further example of a common human degenerative condition where the membrane attack complex is present in a sterile situation and can therefore only damage host tissue. Again, the invention described here will preserve the desirable phagocytosis stimulating aspect of complement, while eliminating the self damaging aspect of the membrane attack complex.

As those skilled in the art will know, these diseases are only examples of many that may be found where the invention described here will have therapeutic benefit.

TABLE 1

The Antibodies using for the experiments.

| Antibody | Company | Dilution/final concentration |
|---|---|---|
| Polyclonal goat anti-sera to Human C1q | Quidel, San Diego, CA | 1/2000 |
| Monoclonal rabbit anti C3d Ab | Quidel, San Diego, CA | 1/2000 |

TABLE 1-continued

The Antibodies using for the experiments.

| Antibody | Company | Dilution/final concentration |
|---|---|---|
| Polyclonal rabbit anti C3d Ab | Dako, Burlington, Ontario | 1/2000 |
| Monclonal mouse anti C4d Ab | Quidel, San Diego, CA | 1/2000 |
| Monoclonal mouse anti C5/C5a Ab | Abcam, Cambridge, MA | 1/2000 |
| Polyclonal rabbit anti C5/C5b Ab | Abcam, Cambridge, MA | 1/2000 |
| Polyclonal Goat anti human C6 Ab | Quidel, San Diego, CA | 1/2000 |
| Polyclonal Goat anti human C7 Ab | Quidel, San Diego, CA | 1/2000 |
| Polyclonal Goat anti human C8 Ab | Quidel, San Diego, CA | 1/2000 |
| Polyclonal Goat anti human C9 Ab | Quidel, San Diego, CA | 1/2000 |
| Monoclonal anti C5b-9 Ab | Dako, Burlington, Ontario | 1/2000 |
| Rabbit anti sheep red blood cell antibody | Cedarlane, Ontario, Canada | 100 µg/ml |
| Mouse anti rabbit IgG antibody | Abnova, Walnut, CA | 100 µg/ml |

What is claimed is:

1. A method of selectively inhibiting the membrane attack complex of complement to treat Alzheimer's disease, the method comprising administering an active ingredient of comprising an effective amount of aurin tricarboxylic acid, aurin quadracarboxylic acid, aurin hexacarboxylic acid, and/or esters thereof, wherein the method excludes administration of components of aurin tricarboxylic acid complex greater than or equal to 1 kilodalton in molecular weight, wherein the Alzheimer's disease is associated with host cell self-damage by the membrane attack complex.

2. A method as claimed in claim 1 wherein the active ingredient consists essentially of an effective amount of aurin tricarboxylic acid.

3. A method as claimed in claim 1 wherein the active ingredient consists essentially of an effective amount of aurin quadracarboxylic acid.

4. A method as claimed in claim 1 wherein the active ingredient consists essentially of an effective amount of aurin hexacarboxylic acid.

5. A method as claimed in claim 1 wherein the active ingredient consists essentially of the respective esters of aurin tricarboxylic acid, aurin quadracarboxylic acid, and/or aurin hexacarboxylic acid.

6. A method as claimed in claim 1 wherein the administering step comprises oral administration.

* * * * *